United States Patent [19]

Casida et al.

[11] Patent Number: 4,985,411
[45] Date of Patent: Jan. 15, 1991

[54] DIALKYL-SUBSTITUTED DITHIANES AND PESTICIDAL COMPOSITIONS

[75] Inventors: John E. Casida, Berkeley, Calif.; Michael Elliott, Aston, England

[73] Assignees: The Wellcome Foundation Ltd., London, England; The Regents of the University of California, Calif.

[21] Appl. No.: 442,629

[22] Filed: Nov. 29, 1989

[30] Foreign Application Priority Data

Nov. 30, 1988 [GB] United Kingdom ............... 8827886

[51] Int. Cl.$^5$ .................. A01N 43/32; C07D 339/08
[52] U.S. Cl. ..................................... 514/63; 514/436; 549/4; 549/20; 549/21; 549/22
[58] Field of Search ..................... 514/436, 63; 549/4, 549/20, 21, 22

[56] References Cited

U.S. PATENT DOCUMENTS 4,640,929  2/1987  Mitsudera et al. ............... 514/436

FOREIGN PATENT DOCUMENTS 0294228  12/1988  European Pat. Off. .
7216230  4/1973  Netherlands .
2203429  10/1988  United Kingdom .

Primary Examiner—Mary C. Lee
Assistant Examiner—Jacqueline Haley
Attorney, Agent, or Firm—Nixon & Vanderhye

[57] ABSTRACT

The present invention provides compounds of the formula (I):

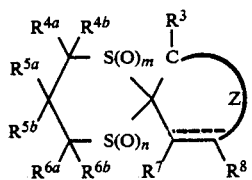

wherein m and n are independently selected from 0, 1 or 2,

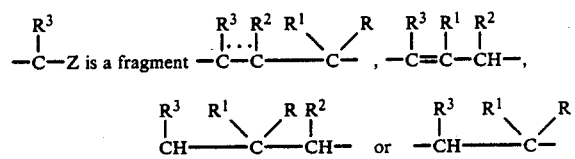

R is selected from hydrogen, methyl or ethyl; $R^1$ is selected from $C_{1-4}$ hydrocarbyl substituted by one to five halo atoms, and a group —C≡C—$R^9$ wherein $R^9$ is a group $S(O)_w$—$R^{10}$ wherein $R^{10}$ is trifluoromethyl, methyl or ethyl and w is 0, 1 or 2 or $R^9$ is a $C_{3-5}$ aliphatic group or an aliphatic group containing up to 5 carbon atoms atoms substituted by $C_{1-4}$ alkoxy, $C_{2-6}$ alkoxyalkoxy, $C_{1-8}$ acyloxy, halo or hydroxy, a group $COR^{11}$ wherein $R^{11}$ is hydrogen, $C_{1-4}$ alkyl, $C_{1-4}$ alkoxy or a group $NR^{12}R^{13}$ wherein $R^{12}$ and $R^{13}$ are independently selected from hydrogen, methyl or ethyl, or $R^9$ is $SiR^{14}R^{15}R^{16}$ wherein $R^{14}$ to $R^{16}$ are the same or different and each is a $C_{1-4}$ aliphatic group or $R^{14}$ and $R^{15}$ are $C_{1-4}$ aliphatic groups and $R^{16}$ is a phenyl group; $R^2$, $R^3$, $R^7$ and $R^8$ are independently selected from hydrogen, methyl or halo; $R^{4a}$ and $R^{4b}$, $R^{6a}$ and $R^{6b}$ are independently selected from hydrogen, $C_{1-3}$ alkyl, $C_{2-3}$ alkenyl or alkynyl each being optionally substituted by halo, cyano or $C_{1-4}$ alkoxy; cyano, halo or a group COR $^{11a}$ wherein $R^{11a}$ is hydrogen, $C_{1-4}$ alkoxy, $C_{1-4}$ alkyl or a group $NR^{12a} R^{13a}$ wherein $R^{12a}$ and $R^{13a}$ are independently selected from hydrogen, methyl or ethyl; $R^{5a}$ is a non-aromatic hydrocarbyl group containing up to seven carbon atoms, or phenyl each optionally substituted by cyano, halo, $C_{1-4}$ alkyl, $C_{1-4}$ haloalkyl, $C_{3-4}$ cycloalkyl, $C_{1-4}$ alkoxy or a group $S(O)_q R^{17}$ wherein q is 0, 1 or 2 and $R^{17}$ is methyl or ethyl and $R^{5b}$ is hydrogen, hydroxy or $C_{1-4}$ alkyl optionally substituted by alkoxy; and represents —CH—CH— or —C═C— which are useful pesticides, processes for their preparation, pesticidal formulations containing them and their use in the control or prevention of pest infestation.

9 Claims, No Drawings

DIALKYL-SUBSTITUTED DITHIANES AND PESTICIDAL COMPOSITIONS

The present invention is concerned with a method of controlling pests such as arthropods, e.g. insects and acarine pests, and helminths, e.g. nematodes, by contacting the pests with novel pesticides. The invention is also concerned with the novel pesticides used for controlling the pests and processes for making such pesticides.

Current classes of pesticides effectively control some but not all pest species. It is also desirable to have new classes of pesticides since pests tend to develop resistance to any one pesticide, or sometimes to any one class of pesticide, after they have been selected with or exposed to such pesticides over a period of time.

Certain 2,5-dialkylsubstituted dithianes have been investigated as liquid crystal materials (see for example Mol. Cryst. Liq. Cryst., 131. 101) but no pesticidal activity has been reported for such compounds.

It has been discovered that a class of novel 1,5-dithiaspirobicycloalkanes has pesticidal activity.

Accordingly, the present invention provides a compound of the formula (I):

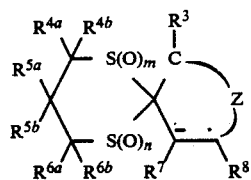

wherein m and n are independently selected from 0, 1 or 2,

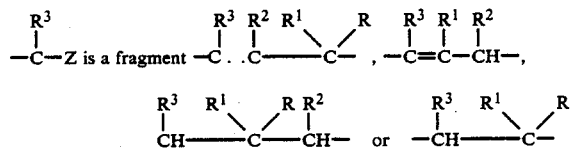

is selected from hydrogen, methyl or ethyl; $R^1$ is selected from $C_{1-4}$ hydrocarbyl substituted by one to five halo atoms, and a group —C≡C—$R^9$ wherein $R^9$ is a group $S(O)_w$—$R^{10}$ wherein $R^{10}$ is trifluoromethyl, methyl or ethyl and w is 0, 1 or 2 or $R^9$ is a $C_{3-5}$ aliphatic group or an aliphatic group containing up to 5 carbon atoms substituted by $C_{1-4}$ alkoxy, $C_{2-6}$ alkoxyalkoxy, $C_{1-8}$ acyloxy, halo or hydroxy, a group $COR^{11}$ wherein $R^{11}$ is hydrogen, $C_{1-4}$ alkyl, $C_{1-4}$ alkoxy or a group $NR^{12}R^{13}$ wherein $R^{12}$ and $R^{13}$ are independently selected from hydrogen, methyl or ethyl, or $R^9$ is $SiR^{14}R^{15}R^{16}$ wherein $R^{14}$ to $R^{16}$ are the same or different and each is a $C_{1-4}$ aliphatic group or and $R^{14}$ and $R^{15}$ are $C_{1-4}$ aliphatic groups and $R^{16}$ is a phenyl group; $R^2$, $R^3$, $R^7$ and $R^8$ are independently selected from hydrogen, methyl or halo; $R^{4a}$ and $R^{4b}$ $R^{6a}$ and $R^{6b}$ are independently selected from hydrogen, $C_{1-3}$ alkyl, $C_{2-3}$ alkenyl or alkynyl each being optionally substituted by halo, cyano or $C_{1-4}$ alkoxy; cyano, halo or a group $COR^{11a}$ wherein $R^{11a}$ is hydrogen, $C_{1-4}$ alkoxy, $C_{1-4}$ alkyl or a group $NR^{12a}R^{13a}$ wherein $R^{12a}$ and $R^{13a}$ are independently selected from hydrogen, methyl or ethyl; $R^{5a}$ is a non-aromatic hydrocarbyl group containing up to seven carbon atoms, or phenyl each optionally substituted by cyano, halo, $C_{1-4}$ alkyl, $C_{1-4}$ haloalkyl, $C_{3-4}$ cycloalkyl, $C_{1-4}$ alkoxy or a group $S(O)_qR^{17}$ wherein q is 0, 1 or 2 and $R^{17}$ is methyl or ethyl and $R^{5b}$ is hydrogen, hydroxy or $C_{1-4}$ alkyl optionally substituted by alkoxy; and ≈ represents —CH—CH— or —C=C—.

By the term "halo" is meant fluoro, chloro, bromo or iodo.

By the term "hydrocarbyl" group is meant an alkyl, cycloalkyl, alkenyl cyclic alkenyl, alkynyl phenyl or naphthyl group or combinations of such groups, for example a cycloalkyl alkyl or phenyl group substituted by an alkynyl group.

By the term "non-aromatic hydrocarbyl group" is meant an alkyl, alkenyl or alkynyl group (including a cyclic alkyl or alkenyl group optionally substituted by alkyl, alkenyl or alkynyl; and alkyl or alkenyl substituted by cyclic alkyl and alkenyl).

Preferably

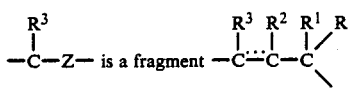

Suitably ≈ represent —C=C—.
Suitably R is methyl
Suitably $R^1$ is a $CCl_3$ or $CHCl_2$ group, or an acetylene group
Suitably $R^2$, $R^3$, $R^7$ and $R^8$ are all hydrogen.
Suitably $R^{4a}$, $R^{4b}$, $R^6$ and $R^{6b}$ are each selected from hydrogen, methyl, cyano or trifluoromethyl and preferably they are all hydrogen.
Suitably $R^{5a}$ is a primary, secondary or tertiary $C_{2-5}$ alkyl group, preferably $R^{5a}$ is t-butyl or i propyl.
Suitably $R^{5b}$ is hydrogen, methyl or ethyl, preferably $R_{5b}$ is hydrogen.

In accordance with yet another embodiment of the present invention there is provided a pesticidal composition containing a compound of the formula (I) in admixture with a diluent or carrier thereof.

Some of the compounds of the formula (I) may exist in a number of stereoisomeric forms. The present invention encompasses both individual conformational and stereoisomers and mixtures thereof. The present invention also encompasses compounds of the formula (I), containing radioisotopes particularly those in which or one to three hydrogen atoms are replaced by tritium or one or more carbon atoms are replaced by $^{14}C$.

Preferred compounds of the invention include:

| Compound Number | Name |
| --- | --- |
| 1 | 3-t-Butyl-9-ethynyl-1,5-dithiaspiro[5.5]undecane |
| 2 | 3-t-Butyl-9-methyl-9-trichloromethyl-1,5-dithiaspiro[5.5]undeca-7,10-diene |
| 3 | 3-t-Butyl-9-dichloromethyl-9-methyl-1,5-dithiaspiro[5.5]undeca-7,10-diene |

The present invention also provides for the preparation of the compounds of the formula (I) by methods derived from those known in the art for the preparation of analogous compounds. Thus, the compounds may be prepared by the reaction of a compound of the formula with suitable ketone of the formula (II):

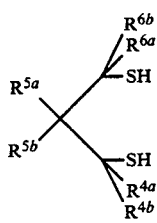

(II)

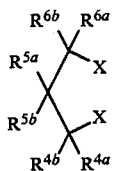

with suitable keynote of the formula
or a reactive derivative thereof, where R to $R^8$ and Z are as hereinbefore defined and, if required, thereafter oxidizing one or both of the ring sulphur atoms.

The reaction is suitably carried out in the presence of a catalyst or of a dehydrating agent in a non-polar solvent at a non-extreme temperature. Suitable catalysts include a dimethyl formamide/dimethyl sulphate catalyst and catalysts such as sulphonic acids or perfluorinated resins thereof or Lewis acids such as boron trifluoride etherate, or stannic chloride or concentrated formic acid which also serves as the reaction medium. Suitable solvents include hydrocarbons such as benzene, toluene or xylene or chlorinated hydrocarbons such as dichloromethane. The reaction is normally performed between 0° and 200° and conveniently between 20° and 120°.

Suitable reactive derivatives of aldehydes and ketones include acetals and ketals.

The compounds of the formula (II) may be prepared from the corresponding diols:

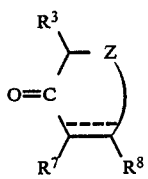

II wherein X is hydroxy via the sulphonate derivatives (i.e., the corresponding compounds wherein X is a group $OSO_2R^{18}$ wherein $R^{18}$ is $C_{1-4}$ alkyl or para-tolyl) as outlined in Appendix 1. The preparation of the diols and their conversion to the corresponding dithiols can be carried out, by methods known in the art for example as outlined in Appendices 1 and 2.

The ketones reacted with the dithiols of the formula (II) are either known in the literature or are prepared by literature methods.

It is often convenient to prepare compounds of the formula (I) by interconversion from other compounds of the formula (I), for example:

(a) By the conversion of a group, for example a group $CH=C(hal)_2$ or $(hal)CH=CH_2$ wherein hal is chloro or bromo, into an ethynyl group. The reaction is conveniently carried out by methods well known to those skilled in the art, for example when the group $-CH=C(hal)_2$ at about or below room temperature, for example between −70° C. and 25° C., in an inert solvent, conveniently an ether such as tetrahydrofuran, using tetrahydrobutyllithium as base.

(b) When it is desired to prepare a compound of the formula (I) wherein $R^9$ is hydrogen by the desilylation of the corresponding tri-$C_{1-4}$ alkylsilylated compound. This reaction may be carried out by methods well known to those skilled in the art, for example by reaction with tetrabutylammonium fluoride in an ether, such as tetrahydrofuran, at a non-extreme temperature, for example between 0° and 70° C. and conveniently at room temperature.

(c) The compounds of the formula (I) may contain two or more sulphur atoms which may be oxidized if required. Oxidations can be carried out by methods well known to those skilled in the art, for example using peracids such as peracetic acid from hydrogen peroxide and acetic acid, or 3-chloroperbenzoic acid in chloroform or dichloromethane, or using periodate such as tetrabutylammonium periodate in a halogenated hydrocarbon, for example chloroform at a non-extreme temperature, for example between 0° and 100° C. and conveniently between 10° and 30° C.

It will be apparent to those skilled in the art that some compounds of the formula (I) may be susceptible to degradation under some of the reaction conditions described above, for example the action of peracids on compounds containing double bonds; these compounds will be prepared by other methods.

The compounds of formula (I) may be used to control pests such as arthropods, e.g. insect and acarine pests, and helminths, e.g. nematodes. Thus, the present invention provides a method for the control of arthropods and/or helminths which comprises administering to the arthropod and/or helminth or to their environment an effective amount of a compound of the formula (I). The present invention also provides a method for the control of arthropod and/or helminth infestations of animals (including humans) and/or of plants (including trees) and/or stored products which comprises administering an effective amount of a compound of the formula (I). The present invention further provides for the compounds of the formula (I) for use in human and veterinary medicine, in public health control and in agriculture for the control of arthropod and/or helminth pests.

By the term "control" is meant the amelioration of present or future deleterious effects of pests and includes killing adults, larvae and eggs, the inhibition of reproduction, the repellency and/or knockdown of pests, and any other influence on behaviour.

Compounds of formula (I) are of particular value in the protection of field, forage, plantation, glasshouse, orchard and vineyard crops, of ornamentals and of plantation and forest trees, for example, cereals (such as maize, wheat, rice, millet, oats, barley, sorghum), cotton, tobacco, vegetables and salads (such as beans, cole crops, cucurbits, lettuce, onions, tomatoes and peppers), field crops (such as potato, sugar beet, ground nuts, soyabean, oil seed rape), sugar cane, grassland and forage crops (such as lucerne), plantations (such as of tea, coffee, cocoa, banana, oil palm, coconut, rubber, spices), orchards and groves (such as of stone and pip fruit, citrus fruits, kiwifruit, avocado, mango, olives and walnuts), vineyards, ornamental plants, flowers and shrubs under glass and in gardens and parks, forest trees (both deciduous and evergreen) in forests, plantations and nurseries and plants grown for industrial or pharmaceutical purposes (such as the evening primrose).

They are also valuable in the protection of timber (standing, felled, converted, stored or structural) from attack by sawflies (e.g. Urocerus) or beetles (e.g. scolytids, platytpodids, lyctids, bostrychids, cerambycids, anobiids).

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

Compounds of formula (I) are of value in the control of public health pests, for example cockroaches and ants.

Compounds of formula I are also of value in the control of arthropods or helminths which are injurious to, or spread or act as vectors of diseases in man and domestic animals, for example those hereinbefore mentioned, and more especially in the control of ticks, mites, lice, fleas, midges biting, nuisance and myiasis flies, mosquitos and hemiptrean bugs.

The compounds of Formula (I) may be used for such purposes by application of the compounds themselves or in diluted form in known fashion as a dip, spray, fog, lacquer, foam, dust, powder, aqueous suspension, paste, gel, cream, shampoo, grease, combustible solid, vaporizing mat, combustible coil, bait, dietary supplement, wettable powder, granule, aerosol, emulsifiable concentrate, oil suspension, oil solution, pressure-pack, impregnated article, microcapsule, pour on formulation or other standard formulations well known to those skilled in the art. Sprays may be applied by hand or by means of a spray race or arch or by vehicle or aircraft mounted apparatus. The animal, soil, plant or other surface being treated may be saturated with the spray by means of high volume application or superficially coated with the spray by means of light or ultra low volume application. Dip concentrates are not applied per se, but diluted with water and the animals immersed in a dipping bath containing the dip wash. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material, such as that against which animals rub and transfer the material to their skins. Pour-on formulations are dispensed as a unit of liquid of small volume on to the backs of animals such that all or most of the liquid is retained on the animals.

Compounds of Formula (I) may be prepared either as formulations ready for use on the animals, plants or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powders and granules and other solid formulations comprise the compound of formula (I) in intimate admixture with a powdered solid inert carrier for example suitable clays, kaolin, bentonite, attapulgite, adsorbent carbon black, talc, mica, silica, chalk, gypsum, tricalcium phosphate, powdered cork, magnesium silicate, vegetable carriers, starch and diatomaceous earths. Such solid formulations are generally prepared by impregnating the solid diluents with solutions of the compound of formula (I) in volatile solvents, evaporating the solvents and, if desired, grinding the products so as to obtain powders and, if desired, granulating, compacting or encapsulating the products.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 99.5% w/v of the composition and may be selected from kerosene, ketones, alcohols, xylene, aromatic naphtha, water, mineral oil, aromatic and aliphatic esters, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates, soaps, lecithins, hydrolysed glues, etc.

Wettable powders comprise an inert solid carrier, one or more surface active agents, and optionally stabilizers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 0.5 to 99.5% by weight of the active ingredient, and are diluted, for example, with water, before use.

Lacquers comprise a solution of the active ingredient in an organic solvent, together with a resin, and optionally a plasticizer.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes, propane, butane, dimethyl ether and the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body. Suitably the plastics material is a polyvinyl chloride (PVC).

The concentration of the compound of formula (I) to be applied to an animal, premises, other substrates or outdoor areas will vary according to the compound chosen, the interval between treatments, the nature of the formulation and the likely infestation, but in general 0.001 to 20.0 w/v and preferably 0.01 to 10% of the compound should be present in the applied formulation. The amount of the compound deposited will vary according to the compound chosen, the method of application, area of application, concentration of the compound in the applied formulation, factor by which the formulation is diluted and the nature of the formulation.

Undiluted formulations such as pour-on formulations in general will be applied at a concentration in the range from 0.1 to 20.0% w/w and preferably 0.1 to 10%. The amount of compound to be applied to stored products in general will lie in the range of from 0.1 to 20 ppm. Space sprays may be applied to give an average initial concentration of 0.001 to 1 mg of compound of formula (I) per cubic meter of treated space.

Compounds of formula (I) are of use in the protection and treatment of plant species, in which case an effective insecticidal, acaricidal or nematocidal amount of the active ingredient is applied. The application rate will vary according to the compound chosen, the nature of the formulation, the mode of application, the plant species, the planting density and likely infestation and other like factors but in general, a suitable use rate for agricultural crops is in the range 0.001 to 3 kg/Ha and preferably between 0.01 and 1 kg/Ha. Typical formulations for agricultural use contain between 0.0001% and 50% of a compound of formula (I) and conveniently between 0.1 and 15% by weight of a compound of the formula (I).

Dusts, greases, pastes and aerosol formulations are usually applied in a random fashion as described above and concentrations of 0.001 to 20% w/v of a compound of Formula (I) in the applied formulation may be used.

The compounds of formula (1) have been found to have activity against the common housefly (*Musca domestica*). In addition, certain compounds of formula (I) have activity against other arthropod pests including *Myzus persicae, Tetranychus urticae, Plutella xylostella,* Culex spp. *Tribolium castaneum, Sitoohilus granarius, Periolaneta americana* and *Blattella germanica*. The compounds of formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. Anobium,Ceutorhynchus,Rhynchoohorus, Cosmopolites, Lissorhoptrus, Meligethes, Hypothenemus, Hylesinus, Acalyvmma, Lema, Psylliodes, Leptinotarsa, Gonocephalum, Agriotes, Dermolepida, Heteronychus, Phaedon, Tribolium, Sitophilus, Diabrotica, Anthonomus or Anthrenus spp.), Lepidoptera (e.g. Ephestia, Mamestra, Earias, Pectinoohora, Ostrinia, Trichoolusia, Pieris, Laohygma, Aorotis, Amathes, Wiseana, Tryporyza, Diatraea, Sporganothis, Cydia, Archips, Plutella, Chilo, Heliothis, Spodootera or Tineola spp.), Diptera (e.g. Musca, Aedes, Anopheles, Culex, Glossina, Simulium, Stomoxys, Haematobia, Tabanus, Hvdrotaea, Lucilia, Chrysomia, Callitroga, Dermatobia, Gasterophilus, Hypoderma, Hylemvia, Atherigona, Chlorops, Phytomyza, Ceratitis, Liriomyza and Melophagus spp.), Phthiraptera (Malophaga e.g. Damalina spp. and Anoolura e.g. Linoqnathus and Haematooinus spp.), Hemiptera (e.g. Aphis, Bemisia,- Phorodon, Aeneolamia, Empoasca, Parkinsiella, Pyrilla, Aonidiella, Coccus, Pseudococcus, Helopeltis, Lygous, Dysdercus, Oxycarenus, Nezara, Aleurodes, Triatoma, Rhodnius, Psylla, Myzus, Megoura, Phylloxera, Adelyes, Niloparvata, Nephrotettix or Cimex spp.), Orthoptera (e.g. Locusta, Gryllus, Schistocerca or Acheta spp.), Dictyoptera (e.g. Blattella, Periolaneta or Blatta spp.), Hymenoptera (e.g. Athalia, Cephus, Atta Lasius, Solenopsis or Monomorium spp.), Isoptera (e.g. Odontotermes and Reticulitermes spp.), Siphonaptera (e.g. Ctenocephalides or Pulex spp.), Thysanura (e.g. Leoisma spp.), Dermaptera (e.g. Forficula spp.), Psocoptera (e.g. Peripsocus spp.) and Thysanoptera (e.g. *Thrips tabaci*),. Acarine pests include ticks, e.g. members of the genera Boophilus, Ornithodorus, Rhipicephalus, Amblyomma, Hyalomma, Ixodes, Haemaohvsalis, Dermacentor and Anocentor, and mites and manges such as Acarus, Tetranychus, Psoroptes, Notoednes, Sarcoptes, Psorergates, Chorioptes, Eutrombicula, Demodex, Panonychus, Bryobia and Eriophyes spp.

Nematodes which attack plants and trees of importance to agriculture, forestry, horticulture, either directly or by spreading bacterial, viral, mycoplasma or fungal diseases of the plants, include root-knot nematodes such as Meloidogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis*); lesion nematodes such as Pratylenchus spp. (e.g. *P. pratensis*); Belonolaimus spp. (e.g. *B. gracilis*); Tylenchulus spp. (e.g. *T. semipenetrans*): Rotylenchulus spp. (e.g. *R. reniformis*); Rotylenchus spp. (e.g. *R. robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. *T. primitivus*): dagger nematodes such as Xiphinema spp. (e.g. *X. diversicaudatum*), Lonoidorus spp (e.g. *L. elongatus*); Hoplolaimus spp. (e.g. *H. coronatus*); Aphelenchoides spp. (e.g. *A. ritzema-bosi, A. besseyi*); stem and bulb eelworms such as Ditylenchus spp. (e.g. *D. dipsaci*).

Compounds of the invention may be combined with one or more other pesticidally active ingredients (for example pyrethroids, carbamates lipid amides and organophosphates) and/or with attractants, repellents, bacteriocides, fungicides, anthelmintics and the like. Furthermore, the activity of compounds of the invention may be enhanced by the addition of a synergist or potentiator, for example: one of the oxidase inhibitor class of synergists, such as piperonyl butoxide, propyl 2-propynylphenyl- phosphonate; a second compound of the invention; or a pyrethroid pesticidal compound. When an oxidase inhibitor synergist is present in a formulation of the invention, the ratio of synergist to compound of Formula (I) will be in the range 500:1–1:25 e.g. about 100:1 to 10:1.

Stabilizers for preventing any chemical degradation which may occur with the compounds of the invention include, for example, antioxidants (such as tocopherols, butylhydroxyanisole and butylhydroxytoluene) and scavengers (such as epichlorhydrin) and organic or inorganic bases e.g. trialkylamines such as triethylamine which can act as basic stabilizers and as scavengers.

The following Examples illustrate, in a non-limiting manner, preferred aspects of the invention.

EXPERIMENTAL

General Synthetic Methods and Procedures

Various compounds were synthesized and characterized in accordance with the following experimental procedures.

$^1$H N.m.r. spectra were obtained on a Bruker AM-250 or WM-300 spectrometer in deuterochloroform solutions with tetramethylsilane as internal standard and are expressed as ppm from TMS, number of protons, number of peaks, coupling constant J Hz.

Mass spectra were obtained on Finnigan 4500 or Hewlett Packard 5985B instruments. Gas-liquid chromatography (g.l.c.) was performed using a Pye Unicam GCD chromatograph fitted with a 3% OV210 column on Gas-Chrom Q and a flame-ionization detector. Progress of reactions could also be conveniently monitored on plastic sheets (40×80 mm) precoated with 0.25 mm layers of silica gel with fluorescent indicator and developed in benzene or in a mixture of hexane and dichloromethane. Temperatures are in degrees Celsius throughout.

The term "processed" is used to mean washing an organic solution with water and brine; drying over magnesium sulphate, and evaporating under reduced pressure.

SECTION 1 PREPARATION OF 1,5-DITHIASPIROALKANES AND ALKENES FROM 1,3-DITHIOLS

Preparation of Intermediates

1. Dithiols (a) 2-t-Butylpropane-1,3-dithiol 2-t-Butylpropane-1,3-diol (E. L. Eliel and Sr. M. C. Knoeber, *J. Amer. Chem. Soc.* 1968, 90, 3444) gave 2-t-butylpropane-1,3-dithiol (E. L. Eliel and R. O. Hutchins, *J. Amer. Chem. Soc.* 1969, 91, 2703)

2. Preparation of 1,5-Dithiaspiroalkanes and alkenes

Example 1

3-t-Butyl-9-(2,2-dibromoethenyl)-1,5-dithiaspiro[5.5]undecane (i) A solution of 4-oxocyclohexanecarboxylic acid (42 g), ethanol (500 ml) and concentrated sulfuric acid (15 ml) was heated at reflux for 6 hours. After cooling, the ethanol was removed under reduced pressure. Water and diethyl ether were added and the solutions separated. The ethereal solution was washed with saturated sodium carbonate solution and processed to give ethyl 4-oxocyclohexanecarboxylate, b.p. 80°–90°/0.2 mmHg (30.6 g).

(ii) A mixture of ethyl 4-oxocyclohexanecarboxylate (3.0 g), ethyleneglycol (2.5 g), p-toluene sulphonic acid (50 mg) and toluene (50 ml) was heated at reflux for 5 hours. The solution was cooled and processed to give ethyl 1,4-dioxaspiro[4.5]-decane-8-carboxylate (2.8 g), b.p. 150°/0.5 mmHg.

(iii) A solution of ethyl 1,4-dioxaspiro[4.5]decane-8-carboxylate (2.7 g) in dry diethyl ether (50 ml) was added dropwise to a stirred suspension of lithium aluminium hydride (1.0 g) in dry diethyl ether (120 ml). The mixture was heated at reflux for 2 hours and cooled. Sodium hydroxide solution (2N,4 ml) was slowly added and the supernatant liquid decanted, and dried over magnesium sulphate. Evaporation gave 1,4-dioxaspiro[4.5]dec-8-ylmethanol (2.3 g) as an oil $n_D$ 1.4818.

(iv) A solution of dimethylsulphoxide (6.4 ml) in dichloromethane (10 ml) was added dropwise to a solution of oxalyl chloride (4.5 ml) in dichloromethane (70 ml) at −60° and stirred under nitrogen over 30 minutes. 1,4-Dioxaspiro[4.5]dec-8-ylmethanol (5.16 g) dissolved in dichloromethane (50 ml) was added over 1 hour. Triethylamine (30 ml) was added at this temperature and the mixture allowed to warm to 0°. Water (100 ml) was added and the organic solution separated and washed successively with dilute hydrochloric acid, saturated sodium hydrogen carbonate solution and processed.

1,4-Dioxaspiro[4.5]decane-8-carboxaldehyde (3.7 g) was obtained as an oil b.p. 130°–140°/0.5 mmHg.

(v) A solution of triphenylphosphine (11.4 g) in dichloromethane (50 ml) was stirred under nitrogen while a solution of carbon tetrabromide (7.2 g) in dichloromethane (50 ml) was added over five minutes. After stirring at 25° for 30 minutes a solution of 1,4-dioxaspiro[4.5]decane-8-carboxaldehyde (3.7 g) in dichloromethane (50 ml) was added dropwise over 30 minutes. The solution was stirred overnight and water added. The organic solution was separated and processed to give after column chromatography on silica eluting with hexane: ether 9:1, the product 8-(2,2-dibromoethenyl)-1,4-dioxaspiro[4.5]decane (1.9 g).

(vi) The above crude ketal (0.5 g) in chloroform (28 ml) was stirred under nitrogen at room temperature. t-Butylpropane-1,3-dithiol (313 l) was added followed by boron trifluoride etherate (0.17 ml). After 2 hours water was added and the solutions separated. The organic phase was processed and 3-t-butyl-9-(2,2-dibromoethenyl)-1,5-dithiaspiro[5.5]undecane (271 mg) crystallized from chloroform : methanol, m.p.=143° Nuclear Magnetic Resonance Spectrum (NMR) was as follows:

0.9 (9H,s); 1.5–2.5(10H,m); 2.7(4H,m); 6.3(1H,d).

EXAMPLE 2

3-t-Butyl-9-ethynyl-1,5-dithiaspiro[5.5]undecane n-Butyllithium (1.6M,0.7 ml) in hexane was added dropwise to a solution of 5-t-butyl-9-(2,2-dibromoethenyl)-1,5-dithiaspiro[5.5]undecane (210 mg) in dry tetrahydrofuran (15 ml) stirred under nitrogen at −40°. The solution was allowed to warm to room temperature and stirred for 4 hours. Water and diethyl ether were added and the solutions separated. The organic phase was processed to give 3-t-butyl-9-ethynyl-1,5-dithiaspiro[5.5]undecane (135 mg). m.p. 86°–7° (hexane).

Example 3

3-t-Butyl-9-methyl-9-trichloromethyl-1,5-dithiaspiro[5.5]undeca-7,10-diene

4-Methyl-4-trichloromethyl-2,5-cyclohexdienone was synthesized without significant variation from the method described by M. S. Newman and A. G. Pinkus, *J. Org. Chem.* 19, 978 (1954) m.p. 103° (from hexane).

To the above ketone (1.34 g) in formic acid (96%, 5 ml) was added 2-t-butyl-propane-1,3-dithiol (1 ml). Solid separated within 30 minutes. After setting aside overnight the reaction mixture was diluted with water (25 ml); the solid product was collected by filtration, washed, dried in vacuo (2.36 g) and recrystallised from ethanol (75–80 ml) to give the above spiro derivative (1.47 g) m.p. 183°.

Example 4

3-t-Butyl-9-dichloromethyl-9-methyl-1,5-dithiaspiro[5.5]undeca-7,10-diene

4-Dichloromethyl-4-methyl-2,5-cyclohexadienone was prepared by the method of K. Auwers and G. Kiel, Ber., 35, 4207 (1902). The yellow oil obtained on steam distillation of the product was collected in ether, dried ($MgSO_4$) and distilled. The upper fraction. b.p. 115°–118° at 2 mm. crystallised on cooling. It was recrystallised from hexane m.p. 46°–48° and further purified by trituration under 4% sodium hydroxide solution (approx. 10 ml/g) and recrystallised from hexane/benzene m.p. 51°–52°.

2-t-Butyl-propane-1,3-dithiol (1 ml) was added to the above ketone (1.16 g) in formic acid (96%, 5 ml). After agitation by sonication for 3 hours the mixture was poured into water (20 ml) and the product was extracted into dichloromethane, washed with saturated $NaHCO_3$ and dried ($MgSO_4$). The viscous residue remaining after removal of solvent was scratched and taken up in hexane. The solid obtained on cooling was twice recrystallised from hexane to give the required product, hard crysalline lumps m.p. 120°.

Example 5

9-Methyl-9-trichloromethyl-1,5-dithiaspiro[5.5]undeca-7,10-diene

The ketone (prepared as in Example 3 above) (1.01 g) was dissolved in formic acid (96%, 5 ml) and propane-1,3-dithiol (0.5 ml) was added. Crystals started to separate after 5 minutes. After 18 hours the reaction mixture was diluted with water, the product (1.47 g) was collected by filtration, washed, dried and recrystallised from ethanol (1.29 g) as long needles m.p. 149°.

Example 6

3-t-Butyl-8,9-dimethyl-9-trichloromethyl-1,5-dithiaspiro[5.5]undeca-7,10-diene 3,4-Dimethyl-4-trichloromethyl-2,5-cyclohexadienone was prepared by condensing 3,4-dimethylphenol with carbon tetrachloride by the procedure of M. S. Newman and L. L. Wood (*J. Amer. Chem. Soc.*, 81, 6450 (1959)) and isolating the product by distillation (b.p. 151°–153°/2 mm) (not steam distillation) following M. S. Newman and F. Bayerlein (J. Org. Chem., 28, 2804 (1963)). After recrystallisation from hexane the product had m.p. 57°.

To the above ketone (1.42 g) in formic acid (96%, 5 ml) was added 2-t-butylpropane-1,3-dithiol (1 ml). The mixture was set aside overnight, then the solid product was isolated by filtration, washed and dried. The solid obtained (1.49 g) was crystallised from hexane (20 ml) to give the above product (0.74 g) m.p. 141°–143° (nmr indicated that the two isomers were present in ratio ca. 0.55 : 0.39;).

Example 7

3-t-Butyl-9-methyl-9-trichloromethyl-1,5-dithiaspiro[5.5]undecane

4-Methyl-4-trichloromethylcyclohexanone (from hydrogenation of the corresponding cyclohexadienone with 10% palladium on charcoal in methanol : H. de Beule, D. Tavernier and M. Anteunis, *Tetrahedron* 30, 3573 (1974)) (0.09 g) in formic acid (to 1 ml) was treated with 2-t-butylpropane-1,3-dithiol (0.06 ml). After 5 minutes the reaction mixture was diluted with water. The solid product was isolated by filtration, washed with water, dried and recrystallised from ethanol (0.09 g., m.p. 162°).

Example 8

3-t-Butyl-9-dichloromethyl-9-methyl-1,5-dithiaspiro[5.5]undecane

4-Dichloromethyl-4-methylcyclohexa-2,5-dienone (0.25 g) was hydrogenated in methanol (15 ml) over 10% palladium on charcoal (tlc control). The catalyst was removed by filtration using filter cel which was washed with methylene chloride. The solvents were evaporated and formic acid (2 ml,96%) and 2-t-butylpropane-1,3-dithiol (0.21 ml) were added to the residue. The required product, which separated almost immediately, was isolated by diluting the reaction mixture with water, filtration and recrystallisation from ethanol (25 ml). Yield 0.25 g, robust fine needles m.p. 163°.

Example 9

3-t-Butyl-9,9-dimethyl-1,5-dithiaspiro[5.5]undecane

By a similar procedure to that used to prepare the 9-dichloromethyl-9-methyl analogue, 4,4-dimethylcyclohoexenone (Aldrich) after reduction gave the required product, m.p. 117°.

BIOLOGICAL ACTIVITY

The activity of the compounds of the invention were tested by dissolving the compounds in acetone (5%) and then diluting in water: 'Symperonic' (94.5%: 0.5%) to give a water emulsion. The solution was then used to treat the following insects.

*Musca Domestica*

20 female Musca were contained in a cardboard cylinder with gauze over either end. Solution containing the compound was sprayed onto the insects so enclosed and mortality assessed after 48 hours at 25° C.

*Plutella xylostella:*

7 Plutella larvae (3rd instar) were sprayed with the solution containing the compound and added to a Chinese cabbage leaf which had been similarly sprayed and left to dry. Mortality was assessed after 2 days at 25° C.

*Diabrotica undecimpunctata:*

Filter paper was sprayed with the solution containing the compound. Seven 2nd instar larvae were then added to the filter paper, together with a cube of artificial diet. Activity was assessed after 48 hours.

The following compounds were active on *M. domestica* at

-continued less then 200 ppm
2,3

The following compounds were active on *P. xylsotella* at less than 1000 ppm
3

The following compounds were active on *D. undecimpunctata* at less than 1000 ppm
3

Topical Application Tests

Lethal Activity Against *Blattella germanica*

The activity of the compounds of the invention against anesthetized male *Blattella germanica* (WRL strain) was demonstrated by the topical application to the test insect of a solution of the compound under test in butanone with the synergist piperonyl butoxide.

The following compounds were active at less than 50 μg/insect
1

The following compounds were active at less than 50 μg/insect
2,3

Appendix 1

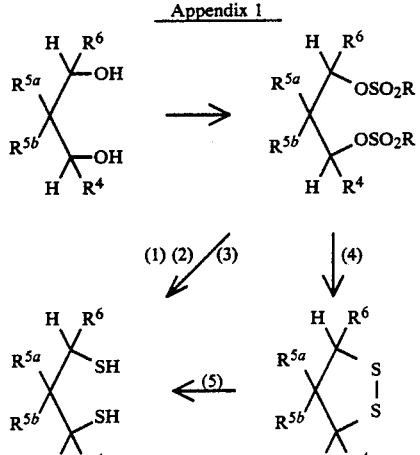

(1) $Na_2CS_3 \cdot H_2O$  (2) HCl  (3) $LiAlH_4$, $Et_2O$
(4) $Na_2S/S$, DMF  (5) $LiAlH_4$, $Et_2O$.

Appendix 2

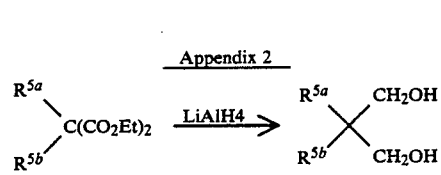

| Formulations | |
|---|---|
| 1. Emulsifiable Concentrate | |
| Compound of formula (I) | 10.00 |
| Alkyl phenol ethoxylate* | 7.50 |
| Alkyl aryl sulphonate* | 2.50 |
| $C_{8-13}$ aromatic solvent | 80.00 |
| | 100.00 |
| 2. Emulsifiable Concentrate | |
| Compound of formula (I) | 10.00 |
| Alkyl phenol ethoxylate* | 2.50 |
| Alkyl aryl sulphonate* | 2.50 |
| Ketonic solvent | 64.00 |
| $C_{8-13}$ aromatic solvent | 18.00 |

-continued

| Formulations | |
|---|---|
| Antioxidant | 3.00 |
| | 100.00 |
| 3. Wettable Powder | |
| Compound of formula (I) | 5.00 |
| $C_{8-13}$ aromatic solvent | 7.00 |
| $C_{18}$ aromatic solvent | 28.00 |
| China clay | 10.00 |
| Alkyl aryl sulphonate* | 1.00 |
| Napthalene sulphonic acid* | 3.00 |
| Diatamaceous earth | 46.00 |
| | 100.00 |
| 4. Dust | |
| Compound of formula (I) | 0.50 |
| Talc | 99.50 |
| | 100.00 |
| 5. Bait | |
| Compound of formula (I) | 0.5 |
| Sugar | 79.5 |
| Parraffin wax | 20.0 |
| | 100.00 |
| 6. Emulsion Concentrate | |
| Compound of formula (I) | 5.00 |
| $C_{8-13}$ aromatic solvent | 32.00 |
| Cetyl alcohol | 3.00 |
| Polyoxyethlene glycerol monooleate* | 0.75 |
| Polyoxyethylene sorbitan esters* | 0.25 |
| Silicone solution | 0.1 |
| Water | 58.9 |
| | 100.00 |
| 7. Suspension Concentrate | |
| Compound of formula (I) | 10.00 |
| Alkyl aryl ethoxylate* | 3.00 |
| Silicone solution | 0.1 |
| Alkane diol | 5.0 |
| Fumed silica | 0.50 |
| Xanthan gum | 0.20 |
| Water | 80.0 |
| Buffering agent | 1.2 |
| | 100.00 |
| 8. Microemulsion | |
| Compound of formula (I) | 10.00 |
| Polyoxyethylene glycerol monooleate* | 10.00 |
| Alkane diol | 4.00 |
| Water | 76.00 |
| | 100.00 |
| 9. Water Dispersible Granules | |
| Compound of formula (I) | 70.00 |
| Polyvinyl pyrrolidine | 2.50 |
| Alkyl aryl ethoxylate | 1.25 |
| Alkyl aryl sulphonate | 1.25 |
| China clay | 25.00 |
| | 100.00 |
| 10. Granules | |
| Compound of formula (I) | 2.00 |
| Alkyl phenol ethoxylate* | 5.00 |
| Alkyl aryl sulphonate* | 3.00 |
| $C_{8-13}$ aromatic solvent | 20.00 |
| Kieselguhr granules | 70.00 |
| | 100.00 |
| 11. Aerosol (pressure pack) | |
| Compound of formula (I) | 0.3 |
| Piperonyl butoxide | 1.5 |
| $C_{8-13}$ saturated hydrocarbon solvent | 58.2 |
| Butane | 40.0 |
| | 100.00 |
| 12. Aerosol (pressure pack) | |
| Compound of formula (I) | 0.3 |
| $C_{8-13}$ saturated hydrocarbon solvent | 10.0 |
| Sorbitan monooleate* | 1.0 |
| Water | 40.0 |
| Butane | 48.7 |
| | 100.00 |
| 13. Aerosol (pressure pack) | |
| Compound of formula (I) | 1.00 |
| $CO_2$ | 3.00 |

-continued

| Formulations | | |
|---|---|---|
| | Polyoxyethylene glycerol monooleate* | 1.40 |
| | Propanone | 38.00 |
| | Water | 56.60 |
| | | 100.00 |
| 14. | Lacquer | |
| | Compound of formula (I) | 2.50 |
| | Resin | 5.00 |
| | Antioxidant | 0.50 |
| | High aromatic white spirit | 92.0 |
| | | 100.00 |
| 15. | Spray (ready to use) | |
| | Compound of formula (I) | 0.10 |
| | Antioxidant | 0.10 |
| | Odourless kerosene | 99.8 |
| | | 100.00 |
| 16. | Potentiated Spray (ready to use) | |
| | Compound of formula (I) | 0.10 |
| | Piperonyl butoxide | 0.50 |
| | Antioxidant | 0.10 |
| | Odourless kerosene | 99.30 |
| | | 100.00 |
| 17. | Microencapsulated | |
| | Compound of formula (I) | 10.0 |
| | $C_{8-13}$ aromatic solvent | 10.0 |
| | Aromatic di-isocyanate# | 4.5 |
| | Alkyl phenol ethoxylate* | 6.0 |
| | Alkyl diamine# | 1.0 |
| | Diethylene triamine | 1.0 |
| | Concentrated hydrochloric acid | 2.2 |
| | Xanthan gum | 0.2 |
| | Fumed silica | 0.5 |
| | Water | 64.6 |
| | | 100.00 |

*Surfactant
# = react to form the polyurea walls of the microcapsule Antioxidant could be any of the following individually or combined Butylated hydroxytoluene Butylated hydroxyanisole Vitamin C (ascrobic acid)

TABLE 1

| Compound Number | Name |
|---|---|
| 1 | 3-t-Butyl-9-ethynyl-1,5-dithiaspiro[5.5]undecane. |
| 2 | 3-t-Butyl-9-methyl-9-trichloromethyl-1,5-dithiaspiro-[5.5]undeca-7,10-diene. |
| 3 | 3-t-Butyl-9-dichloromethyl-9-methyl-1,5-dithiaspiro-[5.5]undeca-7.10-diene. |
| 4 | 9-Methyl-9-trichloromethyl-1,5-dithiaspiro[5.5]undeca-7,1-diene. |
| 5 | 3-t-Butyl-8,9-dimethyl-9-trichloromethyl-1,5-dithiaspiro[5.5]undeca-7,10-diene. |
| 6 | 3-t-Butyl-9-methyl-9-trichloromethyl-1,5-dithiaspiro-[5.5]undecane. |
| 7 | 3-t-Butyl-9-dichloromethyl-9-methyl-1,5-dithiaspiro-[5.5]undecane. |
| 8 | 3-t-Butyl-9,9-dimethyl-1,5-dithiaspiro[5.5]undecane. |

TABLE 2

Nuclear Magnetic Resonance Spetra:- $^1$H, $CDCl_3$, and expressed as ppm. downfield from TMS (number of protons, multiplicity).

| | |
|---|---|
| 1 | 0.9(9H,s); 1.5–2.5(10H,m); 2.1(1H,s); 2.7(4H,m). |
| 2 | 0.9(9H,s); 1.5(3H,s); 1.8(1H,m); 2.8(4H,m); 5.8–6.6(4H,m). |
| 3 | 0.9(9H,s); 1.3(3H,s); 1.8(1H,m); 2.9(4H,m); 5.5(1H,s); 5.5–6.6(4H,m). |
| 4 | 1.5(3H,s); 2.0(2H,m); 2.9(4H,m); 6.0(2H,d); 6.3(2H,d). |
| 5 | 0.9(9H,s); 1.6(3H,s); 1.7(1H,m); 2.1(3H,s); 2.8(4H,m); 5.7–6.6(3H,m). |
| 6 | 0.9(9H,s); 1.85(3H,s); 1.7–2.6(9H,m); 2.8(4H,m). |
| 7 | 0.9(9H,s); 1.1(3H,s); 1.4–2.4(9H,m); 2.8(4H,m); 5.6(1H,s). |
| 8 | 0.9(15H,s); 1.4–2.1(9H,m); 2.7(4H,m). |

TABLE 3

DITHIANES - Further Characterising Data

| Compound Number | Method of Preparation Example Number | Mass Spectrum Chemical Ionisation $M+1$ | M.p. °C. or $N_D$ | Description |
|---|---|---|---|---|
| 1 | 2 | 269 | 86-7 | White Solid |
| 2 | 3 | 371 | 183 | Solid |
| 3 | 4 | 337 | 120 | Hard Crystalline Lumps |
| 4 | 5 | — | 149 | Long Needles |
| 5 | 6 | 385 | 141-3 | Solid |
| 6 | 7 | — | 162 | Solid |
| 7 | 8 | — | 163 | Robust Fine Needles |
| 8 | 9 | 273 | 117 | White Solid |

We claim:

1. A compound of the formula (I):

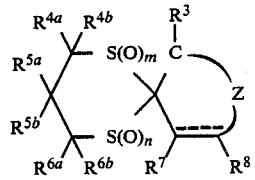

wherein m and n are independently selected from 0, 1 or 2,

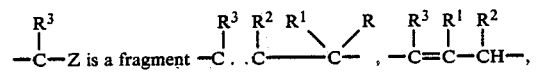
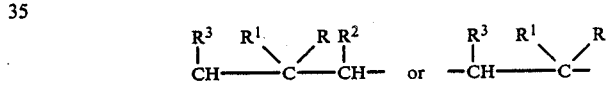

R is selected from hydrogen, methyl or ethyl; $R^1$ is selected from $C_{1-4}$ hydrocarbyl substituted by one to five halo atoms, and a group $-C\equiv C-R^9$ wherein $R^9$ is a group $S(O)_w-R^{10}$ wherein $R^{10}$ is trifluoromethyl, methyl or ethyl and w is 0, 1 or 2 or n is a $C_{3-5}$ aliphatic group or an aliphatic group containing up to 5 carbon atoms substituted by $C_{1-4}$ alkoxy, $C_{2-6}$ alkoxyalkoxy, $C_{1-8}$ acyloxy, halo or hydroxy, a group $COR^{11}$ wherein $R^{11}$ is hydrogen, $C_{1-4}$ alkyl, $C_{1-4}$ alkoxy or a group $NR^{12}R^{13}$ wherein $R^{12}$ and $R^{13}$ are independently selected from hydrogen, methyl or ethyl, or $R^9$ is $SiR^{14}R^{15}R^{16}$ wherein $R^{14}$ to $R^{16}$ are the same or different and each is a $C_{1-4}$ aliphatic group or $R^{14}$ and $R^{15}$ are $C_{1-4}$ aliphatic groups and $R^{16}$ is a phenyl group; $R^2$, $R^3$, $R^7$ and $R^8$ are independently selected from hydrogen, methyl or halo; $R^{4a}$ and $R^{4b}$, $R^{6a}$ and $R^{6b}$ are independently selected from hydrogen, $C_{1-3}$ alkyl, $C_{2-3}$ alkenyl or alkynyl or $C_{1-3}$ alkyl, $C_{2-3}$ alkenyl or alkynyl each substituted by halo, cyano or $C_{1-4}$ alkoxy; cyano, halo or a group $COR^{11a}$ wherein $R^{11a}$ is hydrogen, $C_{1-4}$ alkoxy, $C_{1-4}$ alkyl or a group $NR^{12a}R^{13a}$ wherein $R^{12a}$ and $R^{13a}$ are independently selected from hydrogen, methyl or ethyl; $R^{5a}$ is a non-aromatic hydrocarbyl group containing up to seven carbon atoms, or phenyl or a non-aromatic hydrocarbyl group containing up to seven carbon atoms or phenyl each substituted by cyano, halo, $C_{1-4}$ alkyl, $C_{1-4}$ haloalkyl, $C_{3-4}$ cycloalkyl, $C_{1-4}$ alkoxy or a group $S(O)_qR^{17}$ wherein q is 0, 1 or 2 and $R^{17}$ is methyl or ethyl and $R^{5b}$ is hydrogen, hydroxy, $C_{1-4}$ alkyl or $C_{1-4}$ alkyl substituted by alkoxy; and ⋯ represents —CH—CH— or —C≡C—.

2. A compound according to claim 1 wherein

wherein R to $R^3$, Z and ⋯ are as hereinbefore defined.

3. A compound according to claim 1 wherein $R^1$ is a $CCl_3$ or $CHCl_2$ group, or an acetylene group.

4. A compound according to claim 1 wherein $R^2$, $R^3$, $R^7$ and $R^8$ are all hydrogen.

5. A compound according to claim 1 wherein $R^{4a}$, $R^{4b}$, $R^{6a}$ and $R^{6b}$ are each selected from hydrogen, methyl, cyano or trifluoromethyl.

6. A compound according to claim 1 wherein $R^{5a}$ is a primary, secondary or tertiary $C_{2-5}$ alkyl group.

7. A compound according to claim 1 wherein $R^{5b}$ is hydrogen, methyl or ethyl.

8. An insecticidal or acaricidal composition comprising a compound of formula (I) as defined in claim 1 in admixture with a carrier or diluent.

9. A method for the control of pests comprising application to the pest or to an environment susceptible to pest infestation of a pesticidally effective amount of a compound according to claim 1.

* * * * *